(12) United States Patent
Mizutani et al.

(10) Patent No.: US 7,270,652 B2
(45) Date of Patent: Sep. 18, 2007

(54) INTERLABIAL PAD

(75) Inventors: Satoshi Mizutani, Kagawa (JP);
Wataru Yoshimasa, Kagawa (JP); Yuki Noda, Kagawa (JP)

(73) Assignee: Uni-Charm Corporation, Ehime-Ken (JP)

( * ) Notice: Subject to any disclaimer, the term of this patent is extended or adjusted under 35 U.S.C. 154(b) by 183 days.

(21) Appl. No.: 11/007,667

(22) Filed: Dec. 8, 2004

(65) Prior Publication Data

US 2005/0137561 A1 Jun. 23, 2005

(30) Foreign Application Priority Data

Dec. 9, 2003 (JP) ............... 2003-411078

(51) Int. Cl.
*A61F 13/47* (2006.01)
*B32B 7/02* (2006.01)

(52) U.S. Cl. .................. 604/385.17; 428/218
(58) Field of Classification Search ......... 604/385.17, 604/379, 380, 385.101, 385.201
See application file for complete search history.

(56) References Cited

U.S. PATENT DOCUMENTS

| | | | | | |
|---|---|---|---|---|---|
| 3,905,372 | A | * | 9/1975 | Denkinger | 604/359 |
| 4,595,392 | A | * | 6/1986 | Johnson et al. | 604/385.17 |
| 4,673,403 | A | * | 6/1987 | Lassen et al. | 604/385.17 |
| 5,290,262 | A | * | 3/1994 | Vukos et al. | 604/385.17 |
| 5,919,181 | A | * | 7/1999 | Visscher et al. | 604/387 |
| 6,254,584 | B1 | * | 7/2001 | Osborn et al. | 604/385.17 |
| 6,413,248 | B1 | * | 7/2002 | Mizutani | 604/385.17 |
| 6,802,932 | B2 | * | 10/2004 | Kudo et al. | 156/322 |
| 6,888,046 | B2 | * | 5/2005 | Toyoshima et al. | 604/380 |
| 6,923,795 | B1 | * | 8/2005 | Cantley et al. | 604/385.17 |
| 2001/0000796 | A1 | * | 5/2001 | Osborn et al. | 604/385.17 |
| 2002/0058128 | A1 | * | 5/2002 | Toyoshima et al. | 428/182 |
| 2002/0065497 | A1 | * | 5/2002 | Kolby-Falk | 604/368 |
| 2002/0193765 | A1 | * | 12/2002 | Kudo et al. | 604/378 |
| 2002/0193769 | A1 | * | 12/2002 | Edens et al. | 604/385.17 |
| 2002/0193773 | A1 | | 12/2002 | Edens et al. | |
| 2003/0208178 | A1 | * | 11/2003 | Edens et al. | 604/385.17 |
| 2004/0019335 | A1 | * | 1/2004 | Moder et al. | 604/290 |
| 2004/0024376 | A1 | * | 2/2004 | Ohba | 604/385.17 |
| 2004/0068245 | A1 | * | 4/2004 | Rana et al. | 604/385.17 |
| 2004/0116883 | A1 | * | 6/2004 | Krautkramer et al. | 604/367 |
| 2004/0147893 | A1 | * | 7/2004 | Mizutani et al. | 604/385.17 |

(Continued)

FOREIGN PATENT DOCUMENTS

WO  WO-99/56689 A1  11/1999

(Continued)

*Primary Examiner*—Tatyana Zalukaeva
*Assistant Examiner*—Paula L. Craig
(74) *Attorney, Agent, or Firm*—Darby & Darby

(57) ABSTRACT

It is an object of the present invention to provide an interlabial pad with which the fitting point can be found with ease and without damaging the interior of the labia in the fitting process. By equipping a transmitting region 20, which transmits the feel of a finger to a wearer's body in the thickness direction of an interlabial pad, on the entirety or a part of a belt-shaped region that spans the longitudinal direction central axis of the interlabial pad and extends in the longitudinal direction, an interlabial pad 10, with which the fitting point can be found with ease and without damaging the interior of the labia, can be provided.

18 Claims, 8 Drawing Sheets

U.S. PATENT DOCUMENTS

| | | |
|---|---|---|
| 2004/0147896 A1* | 7/2004 | Mizutani et al. ........ 604/385.17 |
| 2004/0147898 A1* | 7/2004 | Mizutani et al. ........ 604/385.17 |
| 2004/0158219 A1* | 8/2004 | Mizutani et al. ........ 604/385.17 |
| 2004/0167492 A1* | 8/2004 | Mizutani et al. ........ 604/385.17 |
| 2005/0215969 A1* | 9/2005 | Mizutani et al. ........ 604/385.17 |

FOREIGN PATENT DOCUMENTS

| | | | |
|---|---|---|---|
| WO | WO-02/094148 A1 | | 11/2002 |
| WO | WO-02/094158 A1 | | 11/2002 |
| WO | WO-02/094161 A1 | | 11/2002 |
| WO | WO02094153 | * | 11/2002 |
| WO | WO02094159 | * | 11/2002 |
| WO | WO-02/100315 A1 | | 12/2002 |
| WO | WO2004019849 | * | 3/2004 |
| WO | WO2004045476 | * | 6/2004 |

* cited by examiner

INTERLABIAL PAD

CROSS-REFERENCE TO RELATED APPLICATIONS

This application is based upon and claims the benefit of priority from Japanese Patent application No. 2003-411078 filed on Dec. 9, 2003, the entire contents of which is incorporated herein by reference.

1. Field of the Invention

The present invention relates to an interlabial pad that can be fitted readily between the labia.

2. Related Art

Conventionally, sanitary napkins and tampons have been used in general as sanitary items (articles) for women. With regard to sanitary napkins, much effort has been made towards preventing the leakage of menstrual blood from gaps that arise due to poor contact thereof with the vicinity of the ostium vaginae. Also with regard to tampons, since the attributes of these articles cause foreign body sensations and discomfort during fitting and difficulties in fitting on inside the vagina, much effort has been made towards eliminating these inconveniences.

Under such circumstances, sanitary items called interlabial pads have come to be noted in recent years as the sanitary items positioned between sanitary napkins and tampons. This interlabial pad is fitted on by making a part thereof be sandwiched between a woman's labia so as to be in contact with the inner surface of the labia, and, in comparison to a sanitary napkin, the leakage of menstrual blood is prevented due to its highly close contact with the body. Also, since menstrual blood is prevented from dispersing to contact the body widely, sanitation and cleanliness are secured. Furthermore, since an interlabial pad is more compact than a sanitary napkin, it is excellent in fitting sensation, comfortable, and also characteristic of being low in psychological resistance of a wearer during fitting in comparison to a tampon, which is inserted inside the vagina.

However, in comparison to a sanitary napkin, since an interlabial pad is fitted between labia, which are difficult to check visually, it has the drawback of being more difficult to fit than a sanitary napkin. Moreover, when an interlabial pad is not fitted on at an appropriate position, the damage due to leakage of menstrual blood is severe since the size is smaller than that of a sanitary napkin. Also, the possibility for erroneous fitting is higher than that of a tampon.

Patent Document 1 may be cited as describing an arrangement with which an improvement is made in regard to the difficulties of fitting on an interlabial pad. Patent Document 1 discloses an interlabial pad with a structure, in which a protruding part is provided on a face side opposite to the face side that contacts the body, and with this structure, since a wearer can pinch the protruding part with fingers to carry out the fitting process, the fitting is considered to be facilitated in comparison to the case where this protruding part is not provided.

However, with this structure, since the fitting point is searched for by means of the nail tips of a wearer, the fitting process is actually dependent on the wearer's intuition and it is not easy for the wearer to grasp an appropriate fitting point. In particular, when a wearer has long nails or wears artificial nails, it is extremely difficult to fit such a prior-art interlabial pad as described above onto an appropriate location. Also, just pinching the protruding part does not enable a wearer to press the interlabial pad to bring it into adequate close contact with the interior of the labia.

Thus the interlabial pad described in Patent Document 1 is far from an accurate ascertainment of the fitting point so as to facilitate fitting, reduce fitting errors, and achieve adequate contact with the pudendal region. Furthermore, there still remains the possibility of menstrual blood and such to stain the fingertips in the fitting process and this has been a reason for reluctance to using an interlabial pad.

Also, the inventions described in Patent Document 2 and Patent Document 3 disclose an interlabial pad in which a region, on which a finger can be fixed temporarily, is formed on a clothes surface side in order to facilitate the finding of the fitting point using the sensation at the fingertips. In these interlabial pads, a finger can be fixed temporarily on the clothes surface side, and the ostium vaginae position, which is a recessed part, can be searched, across a top sheet, a back sheet, and an absorbent layer, with the fingertip. However, when the absorbing layer and such are thick or rigid, it is difficult to find the accurate position of the ostium vaginae. Also, there is the danger of the interior of the labia to be damaged since the periphery of the ostium vaginae may become rubbed in the process of searching for the ostium vaginae position.

[Patent Document 1] International Patent Publication No. WO99/56689 Pamphlet

[Patent Document 2] International Patent Publication No. WO02/94148 Pamphlet

[Patent Document 3] United States Patent Publication No. 2002/0193773 Specification

SUMMARY OF THE INVENTION

As described above, with conventional interlabial pads, it was difficult to find the fitting point with ease and without damaging the interior of the labia. The present invention has been made in view of these problems and an object thereof is to provide an interlabial pad with which the fitting point can be found with ease and without damaging the interior of the labia.

The present inventors have carried out diligent researches on how to enable the fitting position of an interlabial pad accurately without harming the extremely delicate interior of the labia. As a result, they have found that, by providing, on a part or all of a belt-shaped region that spans a longitudinal direction central axis of an interlabial pad and extends in the longitudinal direction, a transmitting region, which transmits the feel of a finger to a wearer's body in the thickness direction of the interlabial pad, the fitting point can be found readily without harming the interior of the labia and have thus come to complete the present invention. Specifically, the present invention provides the following.

(1) An interlabial pad, having a body side face oriented towards a body side, and an opposite body side face oriented towards the side opposite to the body side face, and being practically formed to a longitudinal shape having a longitudinal direction and a lateral direction; wherein the interlabial pad is equipped with an absorbent which has a predetermined thickness and absorbs and holds body fluids, and to be fitted between labia by a wearer setting a finger on the opposite body side face along the longitudinal direction in the fitting process, and has, on a part or all of a belt-shaped region, spanning a central axis in the longitudinal direction and extending in the longitudinal direction, a transmitting region which transmits the feel of the finger to the wearer's body in the thickness direction of the interlabial pad.

In the interlabial pad according to (1), a transmitting region, which transmits the feel of a finger to a wearer's body in the thickness direction of the interlabial pad, is provided on a part or all of a belt-shaped region, spanning the longitudinal direction central axis of the interlabial pad and extending in the longitudinal direction. In the process of fitting on the interlabial pad, a wearer sets a finger along the transmitting region from the opposite body side face. The finger thus makes contact with the ostium vaginae across the absorbent and other members, and the ostium vaginae can easily sense the feel of the finger such as movements of the finger by a pressure sensation, touch sensation, or warmth or coldness sensation. The ostium vaginae can thus be found easily in the fitting process, and an appropriate fitting state, in which the longitudinal direction central axis of the interlabial pad and the vicinity thereof are set along the vestibular floor of vagina, can be realized. The interlabial pad can thus be fitted in a bilaterally symmetrical manner onto the labial inner walls that are bilaterally symmetrical, and since gaps will not form between the labial inner walls and the pad, the leakage of menstrual blood can be reduced definitely without shifting of the fitting position. Furthermore, since the ostium vaginae can feel the feel of the finger, there is no need to apply an excessive force to the finger in the process of insertion between the labia, and since there is no need to rub the fitting point, the damaging of the interior of the labia can be avoided.

(2) The interlabial pad according to (1), wherein the width of the belt-shaped region is in a range form 5 mm to 70 mm.

The belt-shaped region provided in the interlabial pad according to (2) specifically refers to a region whose width spanning the longitudinal direction central axis is not less than 5 mm and not more than 70 mm, and the transmitting region is disposed in this region. With the interlabial pad according to (2), with which the width of the belt-shaped region is set to not less than 5 mm and not more than 70 mm, when a wearer sets a finger on the opposite body side face of the interlabial pad in the fitting process, at least half or more of the ball of the finger, and, in some cases, half or more of the circumferential length of the finger becomes covered by the belt-shaped region. Since the finger thus becomes surrounded by the both labia across the belt-shaped region, the wearer can be convinced of having been able to fit on the interlabial pad without fail at an appropriate position, thus getting rid of worry that the interlabial pad may fall during the fitting process. The width of the belt-shaped region is preferably in the range of not less than 5 mm and not more than 70 mm, more preferably in the range from 7 mm to 60 mm, and especially preferably in the range from 10 mm to 25 mm. It is not preferable for the width of the belt-shaped region to be less than 5 mm since it will then be difficult for the ostium vaginae to sense the feel of a finger by a pressure sensation, touch sensation, or warmth or coldness sensation. Furthermore, it will not be possible to cover at least half or more of the ball of the finger, and this is not preferable as the wearer will then not be able to feel confident of having been able to fit on the pad at an appropriate position. Also, it is not preferable for the width of the belt-shaped region to be more than 70 mm since it will then be difficult to set the finger along the longitudinal direction central axis of the interlabial pad and it will thus be difficult to fit on the interlabial pad at an appropriate position such that its longitudinal direction central axis and the vicinity thereof are set along the vestibular floor of vagina.

(3) The interlabial pad according to (1) or (2), wherein the transmitting region is lower in the value of linearity of a compression characteristic and thus more easily compressed in the thickness direction by a pressing pressure of the wearer's finger than other regions, which are peripheral regions of the transmitting region.

In the interlabial pad according to (3), the transmitting region is lower in the value of linearity of a compression characteristic (referred to hereinafter as "LC") than the other regions and is thus more easily compressed in the thickness direction. Thus when a pressing pressure of a finger is applied from the opposite body side face of the interlabial pad in the fitting process, the finger sinks in more easily at the transmitting region than at the other regions, and since the thickness of the transmitting region becomes thinner as a result, the feel of the finger can be transmitted to the ostium vaginae more definitely and easily. The ostium vagina is thus found more readily and the interlabial pad can be fitted on definitely and easily at an appropriate position between the labia.

Specifically, the value of the LC at the transmitting region is preferably in the range of not less than 0.10 and not more than 0.50 and more preferably in the range from 0.20 to 0.45. It is not preferable for the value of the LC at the transmitting region to be less than 0.10, since though the feel of the finger can be detected more sensitively by the ostium vaginae, the wearer will be made to feel an aversion (revulsion) due to an excessive sensitivity of detection. It is also not preferable for the value of the LC at the transmitting region to be more than 0.50, since the finger will not sink in readily in the fitting process and it thus becomes difficult to realize an appropriate fitting state wherein the longitudinal direction central axis of the interlabial pad and the vicinity thereof are set along the vestibular floor and also since a foreign body sensation will be felt by the hypersensitive vestibular floor due to the compression rigidity. Furthermore, if the thickness remains thin even upon release of the pressing pressure of the finger, a foreign body sensation may be caused due to the high density. It is thus preferable for the transmitting region to be such that a finger sinks in and the thickness becomes thin while the finger's pressing pressure is being applied and for the transmitting region to become restored to the original thickness when the pressing pressure is released. The above LC values are measured in compliance to a measured method using a KES system.

Meanwhile, the LC value of the other regions is preferably in the range of not less than 0.40 and not more than 0.90 and more preferably in the range from 0.50 to 0.70. When the LC value of the other regions is less than 0.40, since the interlabial pad becomes compressed readily when the interlabial pressure changes due to a change in the posture and such of the wearer, menstrual blood that has been absorbed once cannot be held. It is also not preferable for the LC value of the other regions to be more than 0.90, since the other regions will then become extremely rigid in compression rigidity such that the wearer will be made to feel a foreign body sensation and gaps will form with respect to the inner walls of the labia to cause leakage of menstrual blood.

The pressing pressure of a finger refers to the pressure of the finger that is applied in the direction of the body from the opposite body side face in the process of inserting the interlabial pad between the labia and is approximately 50 $g/cm^2$. The LC value in the present invention is thus a value that is measured under pressurization at 50 $g/cm^2$. Also, the abovementioned LC value is a value that is inclusive of the entirety of the thickness direction interposed between the ostium vaginae and the finger in the fitting process. That is, in the case of an interlabial pad comprising a surface side sheet, an absorbent, and a back face side sheet, this value is inclusive of all of these components. Of these members, the member that has the most influence on the physical characteristic values of the interlabial pad as a whole is the absorbent, and an absorbent within the abovementioned numerical range can be selected suitably. However, the material is preferably a material that is bulky in advance so that a finger can sink in readily when the pressing pressure of the finger is applied in the fitting process. Thus rayon or acetate, which has been subjected to physical embossing, chemical pulp, which has been cross-linked by a cross-linking agent and crimped, or a continuous foam body of cellulose foam or synthetic resin is used singly or combination thereof.

In regard to the factors that facilitate transmission of the feel of a finger to the ostium vaginae, the density of the absorbent at the transmitting region and the thickness thereof are considered to be the main factors. The preferable range of the density of the absorbent in the transmitting region is not less than 0.03 g/cm$^3$ and not more than 0.15 g/cm$^3$. It is not preferable for the density of the absorbent at the transmitting region to be less than 0.03 g/cm$^3$ since the feel of the finger will be transmitted to the ostium vaginae excessively and make the wearer feel aversion (revulsion), and there is also the possibility of damaging the ostium vaginae. Meanwhile, it is also not preferable for the density of the absorbent at the transmitting region to be more than 0.15 g/cm$^3$ since the feel of the finger will not be transmitted adequately to the ostium vaginae in this case.

Also, in regard to the thickness of the transmitting region, the thickness under pressurization at 50 g/cm$^2$ is preferably in the range of not less than 0.5 mm and not more than 10.0 mm and more preferably in the range from 1.5 mm to 6.0 mm. It is not preferable for the thickness of the transmitting region under pressurization at 50 g/cm$^2$ to be less than 0.5 mm since the wearer will then be made to feel aversion (revulsion) and it is not preferable for the thickness to be more than 10.0 mm since it will then be difficult to transmit the feel of the finger to the ostium vaginae.

The thickness of the transmitting region may be made thinner than the thickness of the other regions in advance (see FIG. 18). In this case, since the interlabial pad will contact the vestibular floor softly, the wearer will not feel a foreign body sensation.

(4) The interlabial pad according to any one of (1) to (3), wherein the difference in the values of the linearity of the compression characteristic between the transmitting region and the other regions that are peripheral regions of the transmitting region is in a range from 0.05 to 0.50.

In the interlabial according to (4), the difference in the LC values of the transmitting region and the other regions is within the range of not less than 0.05 and not more than 0.50. By setting the difference in the LC values of these regions within this range, a difference in thickness arises in these regions when a finger's pressing pressure is applied from the opposite body side face in the fitting process, and since the thickness of the transmitting region becomes thin compared to the other regions, the feel of the finger can be transmitted definitely to the ostium vaginae. The ostium vaginae can thus be found readily and the interlabial pad can be fitted on definitely and easily at an appropriate position between the labia.

It is not preferable for the difference in the LC values to be less than 0.05. Since, in this case, the transmitting region and the other regions will not differ much in the degree of sinking of the finger in the fitting process, and also since the feel of the finger thus cannot be transmitted adequately to the ostium vaginae, it becomes difficult to realize an appropriate fitting state in which the longitudinal direction central axis and the vicinity thereof of the interlabial pad are set along the vestibular floor. It is also not preferable for the difference in the LC values to be more than 0.50 since the compression rigidity of the other regions will then be extremely high so that even when the interlabial pressure becomes extremely high, as when the wearer sits on a chair and such the interlabial pad will not undergo a change in compression and will thus make the wearer feel a foreign body sensation.

(5) The interlabial pad according to any one of (1) to (4), wherein in the transmitting region, the absorbent has a space therein so as to be easily compressible.

In the interlabial pad according to (5), the absorbent in the transmitting region has a space therein and is easily compressible. With this interlabial pad, when a finger's pressing pressure is applied from opposite body side face in the fitting process, the finger sinks in due to the squashing and compression of the space provided in the absorbent, and since the thickness of the transmitting region thus becomes thin, the feel of the finger can be transmitted to the ostium vaginae definitely. The ostium vaginae can thus be found easily and the interlabial pad can be fitted on definitely and readily at an appropriate position between the labia.

(6) The interlabial pad according to any one of (1) to (5), wherein the transmitting region is smaller in the value of flexural rigidity and can be bent more easily by the pressing pressure of the wearer's finger than the other regions that are peripheral regions of the transmitting region.

In the interlabial pad according to (6), the transmitting region is lower in the value of flexural rigidity (referred to hereinafter as "B") than the other regions and can be bent more easily by the pressing pressure of the finger of the wearer. Thus when the wearer presses the interlabial pad by the finger from the opposite body side face in the fitting process, the interlabial pad can follow the shape and movement of the finger and the feel of the finger can be transmitted to the ostium vaginae definitely and readily. The ostium vaginae can thus be found easily and the interlabial pad can be fitted on definitely and easily at an appropriate position between the labia.

Specifically the value of B in the transmitting region is preferably within the range of not less than $0.10 \times 10^{-4}$ (N·m$^2$/m) and not more than $4.00 \times 10^{-4}$ (N·m$^2$/m) and more preferably within the range from $0.20 \times 10^{-4}$ (N·m$^2$/m) to $3.00 \times 10^{-4}$ (N·m$^2$/m). When the value of B in the transmitting region is less than $0.10 \times 10^{-4}$ (N·m$^2$/m), though the feel of the finger can be detected sensitively by the ostium vaginae, the interlabial pad will become bent more than necessary. This is not preferable since in this case, when the finger, which is set parallel to the interlabial pad, is directed in the vertical direction, the tip of the fingernail will be directed towards the ostium vaginae in the fitting process and may damage the ostium vaginae. Also, it is not preferable for the value of B in the transmitting region to be more than $4.00 \times 10^{-4}$ (N·m$^2$/m), since it would be difficult for the interlabial pad to follow the shape and movement of the finger, and the flexural rigidity can cause a foreign body sensation to be felt at the hypersensitive vestibular floor. These values of B are measured in compliance to a measurement method using a KES system.

Meanwhile, the value of B in the other regions is preferably within the range from $1.00 \times 10^{-4}$ (N·m$^2$/m) to $8.00 \times 10^{-4}$ (N·m$^2$/m) and more preferably within the range from $2.00 \times 10^{-4}$ (N·m$^2$/m) to $5.00 \times 10^{-4}$ (N·m$^2$/m). It is not preferable for the value of B in the other regions to be less than $1.00 \times 10^{-4}$ (N·m$^2$/m) since the interlabial pad may then bend more than necessary, and, depending on the change in the posture of the wearer, the interlabial pad may become twisted, causing gaps to form with respect to the labial inner wall, thereby causing leakage of menstrual blood. It is also not preferable for the value of B in the other regions to be more than $8.00 \times 10^{-4}$ (N·m$^2$/m) since the flexural rigidity of the other regions will then be extremely high to make the wearer feel a foreign body sensation as well as cause gaps to form with respect to the labial inner wall and thereby causing the leakage of menstrual blood.

For the absorbent in the transmitting region of the interlabial pad according to (6), since it is required that the interlabial pad readily follows the shape and movement of a finger, a raw material of high drape property is preferable. For example, a granular absorbent or an absorbent formed of fibers which contain a lubricant for increasing the slipperiness between fibers, fibers of long fiber length, thin fibers of small fiber diameter, divided fibers, fibers of low molecular orientation, or fibers in which $TiO_2$ or other filler is mixed and such may be used singly or in combinations thereof. Besides these, pulp, chemical pulp, rayon, cotton, acetate, or synthetic fibers and such may be used singly or in combinations as long as the absorbent material having a B value in the abovementioned range can be obtained.

The absorbent that uses such a raw material is formed into sheet by an air laid method, melt blown method, spun lacing method, or papermaking method, etc. Also by performing dot, lattice, or other form of embossing by passing the sheet-form absorbent between rolls and making the embossed area percentage of the transmitting region fall within the range of no less than 0.3% and no more than 30% and the embossed area percentage of the other regions fall within the range of no less than 5% and no more than 50%, the slipperiness between fibers of the transmitting region can be secured. Dot embossing is preferable.

(7) The interlabial pad according to any one of (1) to (6), wherein the difference in the flexural rigidity value between the transmitting region and the flexural rigidity value of the other regions that are peripheral regions of the transmitting region is in a range from $0.50 \times 10^{-4}$ ($N \cdot m^2/m$) to $5.00 \times 10^{-4}$ ($N \cdot m^2/m$).

In the interlabial pad according to (7), a difference in the B value is set between the transmitting region and the other regions. By setting a difference in the B values of these regions, the respective regions are made to differ in the degree to which the interlabial pad follows the shape and movement of a finger, and the feel of the finger can thus be transmitted definitely to the ostium vaginae. The ostium vaginae can thus be found easily and the interlabial pad can be fitted on definitely and easily at an appropriate position between the labia.

Specifically, the difference in the B values of the transmitting region and the other regions is within the range of not less than $0.50 \times 10^{-4}$ ($N \cdot m^2/m$) and not more than $5.00 \times 10^{-4}$ ($N \cdot m^2/m$). When the B value difference is less than $0.50 \times 10^{-4}$ ($N \cdot m^2/m$), since the transmitting region and the other regions will not differ in the degree to which the interlabial pad follows the shape and movement of a finger, the feel of the finger will not be transmitted adequately to the ostium vaginae and it becomes difficult to realize an appropriate fitting state in which the longitudinal direction central axis and vicinity thereof of the interlabial pad are set along the vestibular floor. Also, it is not preferable for the B value difference to be more than $5.00 \times 10^{-4}$ ($N \cdot m^2/m$) since the flexural rigidity of the other regions will then be very high with respect to the extremely delicate labial inner wall and this will make the wearer to feel a foreign object sensation and gaps to form with respect to the labial inner walls, thereby causing leakage of menstrual blood.

(8) The interlabial pad according to any one of (1) to (7) wherein the transmitting region has slits.

In the interlabial pad according to (8), the interlabial pad has been subjected to a slitting process at the transmitting region in order to make it easily bendable. By thus applying a slitting process to the transmitting region and making it readily bendable, the interlabial pad is made to follow the shape and movement of a finger definitely and the feel of the finger can be transmitted to the ostium vaginae definitely. The ostium vaginae can thus be found easily and the interlabial pad can be fitted on definitely and readily at an appropriate position between the labia.

Specifically in order to make the interlabial pad bend easily in the longitudinal direction, it is preferable to provide the absorbent with a slit pattern that is directed in the lateral direction, and in order to make the interlabial pad bend readily in the lateral direction, it is preferable to provide the absorbent with a slit pattern that is directed in the longitudinal direction. Also, a slit pattern that is directed in the lateral direction may be combined or crossed with a slit pattern that is directed in the longitudinal direction or the slit pattern may be one that is directed in a diagonal direction. The shape of the slits may be linear, curved, wave-like, and such, and is not restricted in particular. The slits preferably have a dimension in the range of not less than 1 mm and not more than 20 mm and the interval between slits is preferably set in the range of not less than 1 mm and not more than 20 mm. These slits may be formed to pass through in the thickness direction or may be formed so as not pass through in the thickness direction. Though embossing may be applied instead of slitting, since an embossment becomes a starting point for bending so as to become highly dense and may thus make a wearer feel a foreign body sensation, therefore slitting is more preferable.

(9) The interlabial pad according to any one of (1) to (8), wherein the interlabial pad comprises a surface side sheet positioned at the body side face, and a back face side sheet positioned at the opposite body side face, and at the transmitting region, the absorbent and the surface side sheet or the absorbent and the back face side sheet are in a state of being free of each other entirely or in part.

At the transmitting region of the interlabial pad according to (9), the absorbent and the surface side sheet or the absorbent and the back face side sheet are not joined to each other entirely or in part and are in a state of being free of each other entirely or in part. By thus providing a part at which the absorbent and the surface side sheet or the absorbent and the back face side sheet are not joined to each other, the respective members can move independently, and since the interlabial pad is thereby made easily bendable as a whole, the interlabial pad will follow the shape and movement of a finger and the feel of the finger can be transmitted to the ostium vaginae definitely. The ostium vaginae can thus be found readily and the interlabial pad can be fitted on definitely and readily at an appropriate position between the labia.

Methods of making an interlabial pad easily bendable include not only methods of adjusting the physical properties of the absorbent and methods of adjusting the conditions of joining of the surface side sheet, back face side sheet, and absorbent but also methods of providing bendability to the surface side sheet and the back face side sheet themselves in the transmitting region. Specifically, the surface side sheet and the back face side sheet can be made easily bendable by providing extensibility by applying a slitting process or wave-like engagement embossing process thereto.

However, if slitting process is applied to the surface side sheet, the end parts of slits may contact and irritate the vestibular floor and a wearer may thus be made to feel a foreign object sensation, and if slitting process is applied to the back face side sheet, leakage of menstrual blood may occur. It is thus preferable to apply a wave-like engagement embossing process to the surface side sheet and the back face side sheet themselves. This is preferable since not only is the interlabial pad as a whole is made readily bendable, but the interlabial pad as a whole becomes easily compressible in the thickness direction as well since the surface side sheet and the back face side sheet are provided with extensibility and sink in readily by finger pressure even when a easily compressible absorbent is equipped.

(10) The interlabial pad according to any one of (1) to (9), wherein the transmitting region is higher in thermal conductivity than the other regions that are peripheral regions of the transmitting region.

The transmitting region of the interlabial pad according to (10) is higher in thermal conductivity than the other regions. Thus when a wearer applies a pressing pressure by a finger from the opposite body side face in the fitting process, the body heat from the finger can be conducted to the ostium vaginae at the transmitting region. The ostium vaginae can thus be found easily and the interlabial pad can be fitted on definitely and readily at an appropriate position between the labia.

The thermal conductivity of the transmitting region can be made high by lessening the amount of air that is retained between the ostium vaginae and a finger when a pressing pressure is applied by the finger from the opposite body side face in the fitting process. As a specific example, the thermal conductivity can be made high by lessening the thickness or by increasing the density of the interlabial pad. The optimal thickness and density of the transmitting region have been the same as described above.

The thermal conductivity of the transmitting region can also be made high by selecting a raw material of high thermal conductivity as the absorbent in the transmitting region. Though copper, aluminum, diamond, carbon and such can be cited as generally known raw materials that are high in thermal conductivity, crushed carbon is preferably used in consideration of the interlabial pad being one with flexibility. It is preferable for this carbon to be activated carbon in that a deodorizing effect is provided in addition to a high thermal conductivity. When carbon is used, it may be used blended in a highly absorbent resin. Also, since, compared to pulp, rayon, and other cellulose-based fibers, synthetic fibers, such as polyethylene, polypropylene and nylon-6, and other synthetic fibers are high in thermal conductivity, these fibers may be used. Specific cases include cases where synthetic fibers are used as the absorbent in the transmitting region while cellulose-based fibers are used as the absorbent in the other regions, and cases where more synthetic fibers are used in the transmitting region than in the other regions, etc. In consideration of the absorbing ability of the absorbent, the combined use of synthetic fibers and rayon as the absorbent in the transmitting region is preferable.

(11) The interlabial pad according to any one of (1) to (10), wherein the transmitting region is positioned at one side in the longitudinal direction so as to be biased towards the side facing the buttocks when the interlabial pad is fitted on.

In the interlabial pad according to (11), the transmitting region is positioned at one side in the longitudinal direction of the interlabial pad so as to be biased towards the side facing the buttocks when the interlabial pad is fitted on. To begin with, the ostium vagina exists at the rearmost part between the labia as viewed by a wearer. Thus by positioning the transmitting region at one side in the longitudinal direction of the interlabial pad so as to be biased towards the side facing the buttocks when the interlabial pad is fitted on, the interlabial pad can be fitted on definitely and readily at an appropriate position between the labia.

Also with this interlabial pad, the region of the interlabial pad that is exposed from the rear of the labia as viewed by a wearer can be reduced. Since an interlabial pad, to begin with, is to be fitted onto a body by the sandwiching force between the labia, the region that is exposed from between the labia contacts the pudendum, and when an impact is applied to the region in contact with the pudendum due to a change in the movement of a wearer and this impact is transmitted to the region that is fitted between the labia, the interlabial pad will fall off from between the labia. Thus by reducing the region of the interlabial pad that is exposed from the rear of the labia, the falling off of the interlabial pad from between the labia can be prevented and consequently, the leakage of menstrual blood can also be reduced.

Specifically, the transmitting region is positioned within the range of not less than 10% to not more than 50% of the total length in the longitudinal direction of the interlabial pad from the end part at the side facing the buttocks when the interlabial pad is fitted on. At less than 10%, the fingertip may protrude beyond the end part of the interlabial pad in the insertion process, thus making it difficult to fit on the interlabial pad at an appropriate position. Also at more than 50%, the region of the interlabial pad that becomes exposed from the rear of the labia becomes large and the interlabial pad falls off readily.

(12) The interlabial pad according to any one of (1) to (11), wherein the transmitting region has an indentation, directed towards the body side face, provided on the opposite body side face.

The transmitting region of the interlabial pad according to (12) has a structure in which an indentation is provided on the opposite body side face. In this interlabial pad, when a finger is set on the opposite body side face in the fitting process, the finger can find the indentation easily to be thus guided to the transmitting region. Since the feel of the finger can thus be transmitted definitely to the ostium vaginae, the interlabial pad can be fitted on definitely and readily at an appropriate position between the labia.

This indentation has a depth in the range of not less than 0.5 mm and not more then 5.0 mm. When the depth of the indentation is less than 0.5 mm, it is not preferable since it will be difficult for a finger to find the position at which the transmitting region is provided in the fitting process. When the depth of the indentation is more than 5.0 mm, it is not preferable since a finger that has been set parallel to the interlabial pad in the fitting process becomes directed in the vertical direction and the ostium vaginae may thus be damaged by the tip of the nail.

(13) The interlabial pad according to any one of (1) to (12), wherein the interlabial pad is folded in two along a crease extending along the longitudinal direction central axis, so that the inside areas of the opposite body side face are faceing each other and joined across a predetermined length along the central axis at a predetermined distance away from the crease, and the transmitting region is positioned in a region in which the inside areas of the opposite body side face are separated each other.

In the interlabial pad according to (13), the inside areas of the opposite body side face, which is positioned at the side in the longitudinal direction that does not face the buttocks when the interlabial pad is fitted on, are joined each other along a predetermined length along the longitudinal direction central axis. Meanwhile, the region, in which the transmitting region is positioned and the inside areas of the opposite body side is not joined each other are positioned so as to be biased towards the side in the longitudinal direction that faces the buttocks. Here, "joined across a predetermined length" means that the inside areas of the opposite body side face are joined to each other across a predetermined length from the side that does not face the buttocks so that the region in which the inside areas of the opposite body side face are not joined to each other will be biased towards the side facing the buttocks when the interlabial pad is fitted on.

A step thus forms between the region in which the inside areas of the opposite body side face are joined each other and the region in which the inside areas of the opposite body side face are not joined t each other so that when a wearer sets a finger on the opposite body side face in the fitting process, the step can be found easily by the finger and the finger can thus be guided readily to the transmitting region. Since the feel of the finger can thus be transmitted definitely to the ostium vaginae, it can be found readily and the interlabial pad can be fitted on definitely and readily at an appropriate position between the labia. Furthermore, since the position, at which the inside areas of the opposite body side face are joined each other, is separated from the crease by a predetermined distance and a space is thus formed between the crease and the joined position, external pressures, which are generated against the interlabial pad during fitting, can be cushioned by this space and thus a wearer will hardly feel a foreign object sensation.

(14) The interlabial pad according to any one of (1) to (13), wherein the interlabial pad is an interlabial pad for urinary incontinence as well.

The interlabial pad according to (14) can be used as an absorbing pad for urinary incontinence. That is, since both the, ostium vaginae, which discharges menstrual blood, and the urethral meatus (openings), which discharges urine, are positioned between the labia, when the interlabial pad according to (14) is used by sandwiching it between the labia, urine can be absorbed. Thus in the interlabial pad according to (14), since urine can be absorbed from between the labia and especially in the vicinity of the urethral meastus, an absorbing pad, which is effective for urinary incontinence, especially urinary incontinence of a light degree, can be provided.

(15) The interlabial pad according to any one of (1) to (14), wherein the interlabial pad is an interlabial pad for absorbing vaginal discharge.

The interlabial pad according to (15), the interlabial pad can be used for absorbing vaginal discharge. That is, since the interlabial pad according to (15) is used upon being sandwiched between the labia and can absorb secreted matter (vaginal discharge) besides the menstrual blood from the ostium vaginae, it can be used for other uses (absorption of vaginal discharge). Thus with the interlabial pad according to (15), since the discomfort of a wearer can be alleviated by the absorbing of vaginal discharge, it is effective for wearer even at times other than during menstruation.

With the interlabial pad according to the present invention, the fitting point can be found easily and without damaging the interior of the labia in its fitting process.

BRIEF DESCRIPTION OF THE DRAWNGS

DESCRIPTION OF THE PREFERRED EMBODIMENT

Embodiments of the present invention shall now be described with reference to the drawings. In the description of embodiments besides the first embodiment, the description of arrangements, actions, and effects that are in common to those of the first embodiment shall be omitted.

First Embodiment

[Overall Constituttion of an Interlabial Pad]

Figure 1:
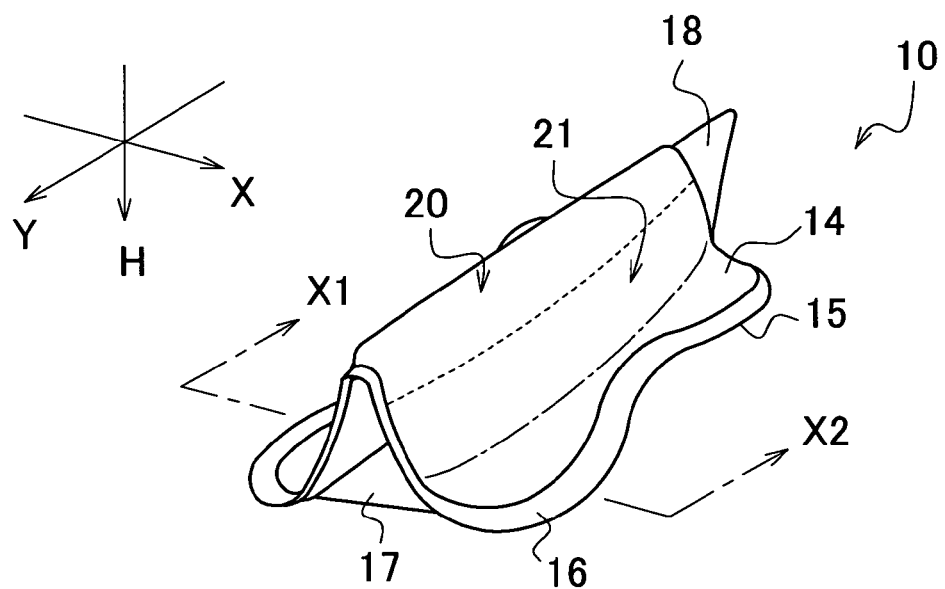
FIG. 1 is a perspective view of an interlabial pad 10 of a first embodiment.

As shown in FIG. 1, the interlabial pad 10 according to this embodiment has a practically longitudinal shape, that is, a substantially gourd-like shape having the Y-axis as the longitudinal direction and the X-axis as the lateral direction as viewed from directly above. Also, the interlabial pad 10 of this embodiment is of a type to be used as folded inward in two along a crease extending along a central axis in the longitudinal direction so that the inside areas of a back face side sheet 15 are facing each other.

Figure 2:
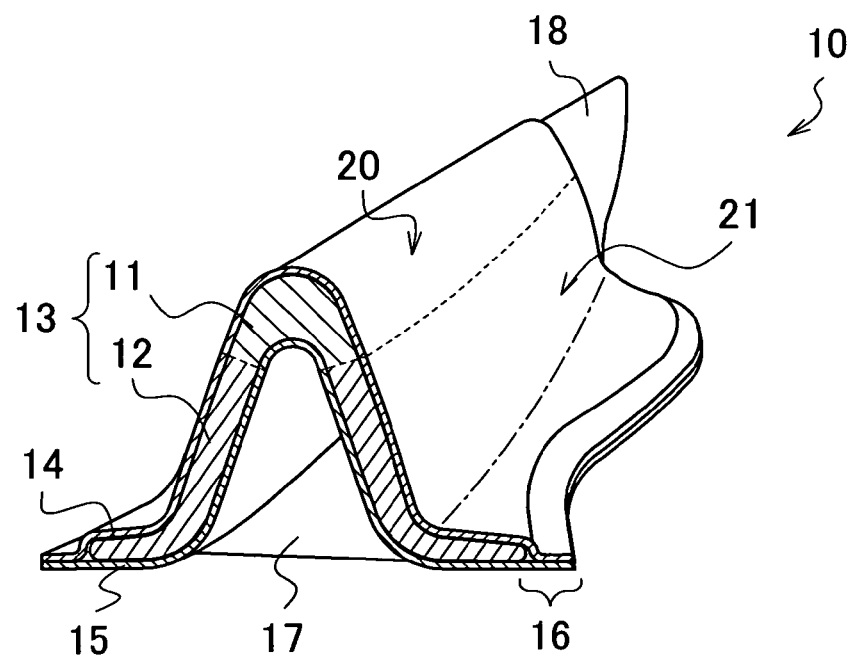
FIG. 2 is a sectional perspective view of the interlabial pad 10 of FIG. 1 as sectioned in the X1-X2 direction.

FIG. 2 is a sectional perspective view, showing the interlabial pad 10, shown in FIG. 1, as sectioned in the X1-X2 direction. The interlabial pad 10 has a surface side sheet 14 and the back face side sheet 15, and between the surface side sheet 14 and the back face side sheet 15 is positioned an absorbent 13. In a belt-shaped region, which spans the longitudinal direction central axis and extends in the longitudinal direction, are disposed a transmitting region 20, which transmits the feel of a finger in the thickness direction of the interlabial pad 10 to a wearer's body, and other regions 21, which are peripheral regions of transmitting region 20.

The surface side sheet 14 is a liquid-permeable sheet that allows the permeation of body fluids of a wearer, and the back face side sheet 15 is a liquid-impermeable sheet that practically does not allow the permeation of body fluids of a wearer. The absorbent 13 comprises a first absorbent 11 at the transmitting region 20 and second absorbents 12 at the other regions 21. Also in addition to there being provided a peripheral part 16, comprising the outer edge of the absorbent 13, surface side sheet 14, and back face side sheet 15, a tab 18 which is pinched by a wearer in taking out the interlabial pad 10 from the labia, is provided. Furthermore, a mini sheet piece 17 forming a finger insertion part is provided so as to bridge opposing sides of the back face side sheet. However, this mini sheet piece 17 is not essential, and an embodiment wherein the mini sheet piece 17 is not provided may also be employed. With an embodiment in which the mini sheet piece 17 is not provided, the inconvenience that, after the fitting on of the interlabial pad at an appropriate position, the fitting position of the interlabial pad becomes shifted in the process of drawing out a finger that has been set on the interlabial pad can be avoided.

Generally for the surface side sheet, a raw material which is liquid-permeable, hydrophilic, and does not irritate the skin, is used. Examples include materials in which non-woven fabrics, obtained by point bonding, air through method, or other manufacturing method, are used singly or in combination thereof as a composite. Among such materials, a sheet, formed mainly of at least cellulose-based hydrophilic fibers, is preferably used in consideration of the compatibility with the labial inner walls so that a wearer will not feel a foreign object sensation due to a deviation arising between the interlabial pad 10 and the labial inner walls.

Specifically, as the surface side sheet 14, a spun-lace non-woven fabric, formed by adjusting fibers, in which natural cotton of a proportion of no less than 5% and no more than 30% is mixed with rayon or acetate of a proportion of no less than 70% and no more than 95%, to be within the range of not less than 20 $g/m^2$ and not more than 50 $g/m^2$ in the basis weight per unit area, entangling the fibers by water entanglement, then drying, and adjusting the thickness to be within the range of not less than 0.3 mm and not more than 1.0 mm, is used. In regard to the yarn quality, for the natural cotton, the fiber length is within the range from 15 mm to 60 mm, and for the rayon or acetate, the fiber length is within the range from 25 mm to 51 mm and the fineness is within the range from 1.1 dtex to 6.6 dtex. A sheet with permeation pores, prepared from a film having permeation pores or by laminating a fiber layer onto a film, may also be used.

As the back face side sheet 15, a sheet of low water permeability is used, and, for example, a film, non-woven fabric, paper and laminate film, prepared by laminating the above may be used, which are composed of polyethylene, polypropylene, polyethylene terephthalate, polyvinyl alcohol, polylactic acid, or polybutyl succinate with a thickness of not less than 15 μm and not more than 60 μm is used as the material. Also, a breathable film, obtained by filling it with an inorganic filler and applying a drawing process, may be used instead. As a specific example, a film, formed mainly of low-density polyethylene (LDPE) resin, having open pores with pore diameters of no less than 0.1 mm and no more than 0.6 mm at a porosity of not less than 10% and not more than 30%, and adjusted to a basis weight per unit area of not less than 15 $g/m^2$ and not more than 35 $g/m^2$, can be cited. Examples of non-woven fabrics are spun-bonded non-woven fabrics, point-bonded non-woven fabrics, through-air non-woven fabrics and such, and these may be finished for water repellency. Among these, three-layered spun-bonded/melt-blown/spun-bonded (SMS) non-woven fabric that includes a melt-blown fabric formed of ultrafine fibers and having an extremely small interfiber distance, is preferable. In this case, the basis weight per unit area of the respective layers are preferably set to be in the ranges from 5 $g/m^2$ to 15 $g/m^2$, from 1 $g/m^2$ to 10 $g/m^2$, and from 5 $g/m^2$ to 10 $g/m^2$, respectively.

[Transmitting Region]

The transmitting region 20 of the interlabial pad 10 according to the present embodiment has an LC value that is lower than that of the other regions 21 and is thus readily compressed in the thickness direction by the pressing pressure of a wearer's finger. Specifically, as the first absorbent 11 in the transmitting region 20, a material, formed by mixing 85% rayon with 15% natural cotton, adjusting the basis weight per unit area to 180 $g/m^2$, and embossing to an emboss area percentage of 1%, is used. For the second absorbents 12 of the other regions 21, a material, formed by mixing 85% rayon with 15% natural cotton, adjusting the basis weight per unit area to 360 $g/m^2$, and embossing to an emboss area percentage of 40%, is used. Whereas the LC value of the transmitting region 20 is 0.41, the LC value of the other regions 21 is 0.63, and the difference between the LC values of the respective regions is 0.22.

Figure 6:
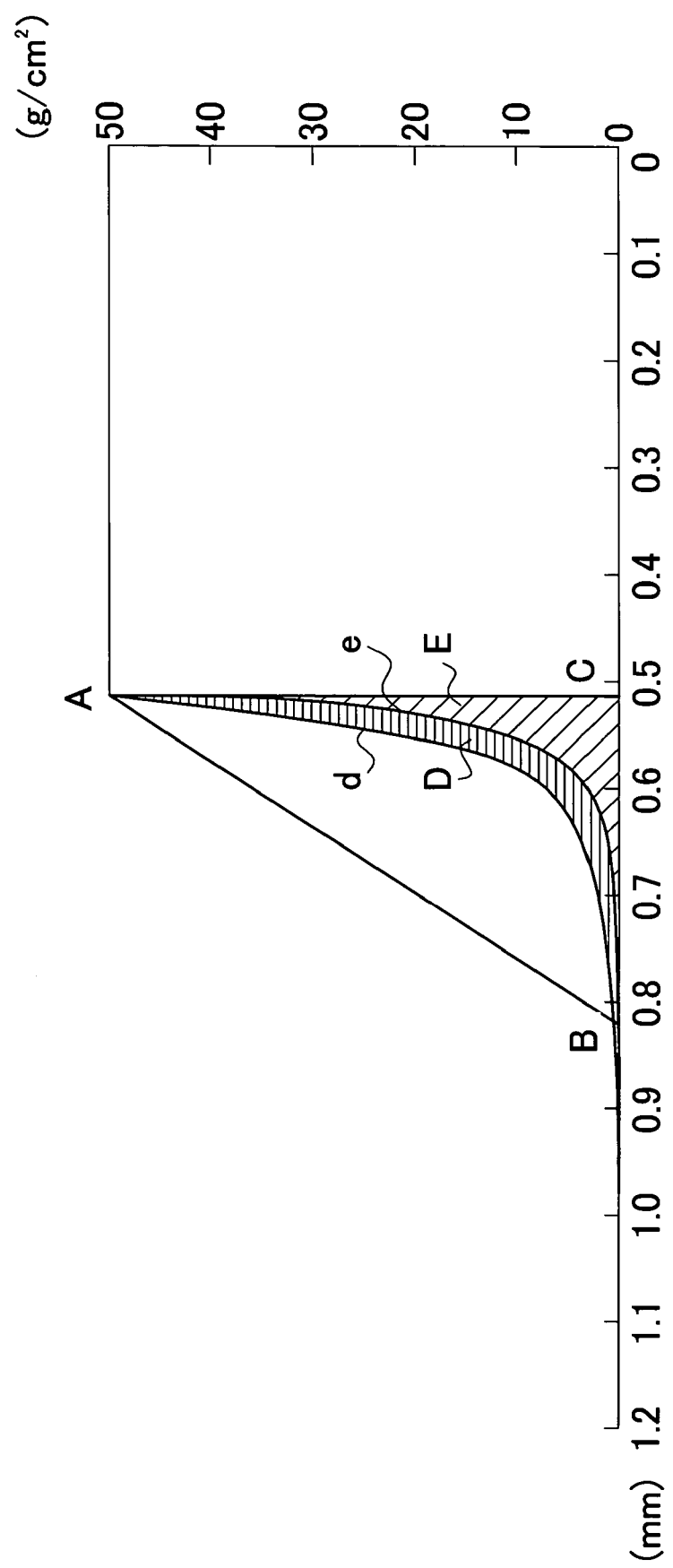
FIG. 6 is a diagram showing a compression characteristic as determined by KES.

Each of these LC values is a value measured in compliance to a measurement method using a KES system and is measured using a "KES Compression characteristic" measuring device made by Kato Tech Co., Ltd. and under the conditions of a load of 50 $g/cm^2$, a compression terminal area of 2 $cm^2$, and a terminal velocity of 0.1 cm/sec. FIG. 6 is a diagram illustrating the KES compression characteristic in a general manner and, here, the abscissa represents the pressure ($g/cm^2$) and the ordinate represents the thickness (mm) of the sample when pressure is applied to the sample. In FIG. 6, the curve "d" shows plots of the relationship between the pressure and the sample thickness as pressure is applied to the sample and the curve "e" shows plots of relationship between the pressure and the sample thickness as the sample is relieved of pressure. The value, determined by dividing the sum of the area of the region D, surrounded by the curve "d" and the curve "e" in this plot diagram, and the area of the region E, surrounded by the curve "e" and the straight lines AC and BC, by the area of the triangle ABC, corresponds to being the LC value.

The size and sampling position of a test piece shall now be described. The size of a test piece is not restricted in particular as long as it is of a size that can accommodate a compression terminal and, for example, a test piece of a size of 30 mm×30 mm is used. The sampling position for a test piece for the transmitting region 20 is a region, which spans the longitudinal direction central axis and comes in contact with the ostium vaginae, and the sampling position for a test piece for the other regions 21 is a region in the periphery of the transmitting region. In the case where the interlabial pad 10 is folded in two, the measurement is carried out in the state in which the interlabial pad 10 is unfolded.

[Actions]

Figure 3:
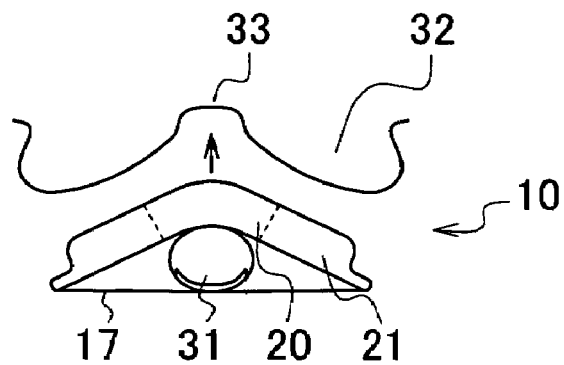
FIG. 3 is a diagram showing a manner in which the interlabial pad 10 of the first embodiment is about to be fitted between labia as viewed from the buttocks side of a wearer.
Figure 4:
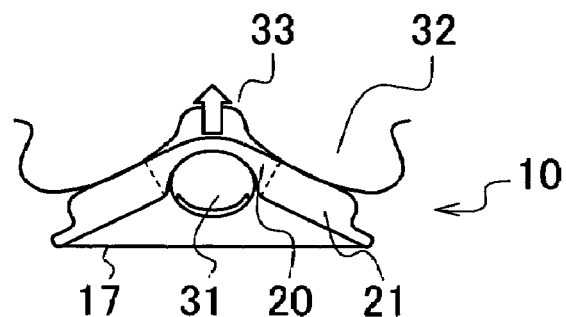
FIG. 4 is a diagram showing a manner in which the interlabial pad 10 of the first embodiment is pushed in between labia as viewed from the buttocks side of a wearer.
Figure 5:
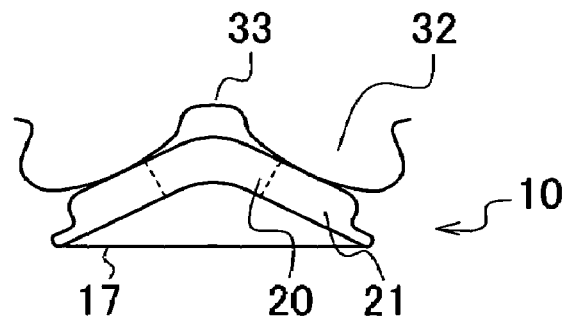
FIG. 5 is a diagram showing a manner in which the fitting on of the interlabial pad 10 of the first embodiment is completed as viewed from the buttocks side of a wearer.

FIG. 3 is a diagram showing the manner in which a wearer sets a finger 31 on the interlabial pad 10 according to the present embodiment with the transmitting region 20 and is about to fit the interlabial pad 10 onto the labia 32 as viewed from the buttocks side of a wearer. In the interlabial pad 10 of this embodiment, since the transmitting region 20 is smaller in LC value than the other regions 21 and is thus more readily compressed in the thickness direction by the pressure of the wearer's finger 31, the transmitting region 20 sinks in by the application of the pressure of the finger 31 from the opposite body side face of the interlabial pad 10 and the thickness of the transmitting region 20 is thereby made thin. The state, in which this occurs, as viewed from the buttocks side of the wearer, is shown in FIG. 4. Also, when the pressure of the finger 31 is relieved, the transmitting region 20 returns to its original thickness. The state, in which this occurs, as viewed from the buttocks side of the wearer, is shown in FIG. 5.

The interlabial pad 10 is fitted on between the labia with the wearer setting a finger on the back face side sheet 15, and in regard to the manner in which the finger is set on the interlabial pad 10 in this process, the finger may not only be set parallel to the vestibular floor but it may be set perpendicular to the vestibular floor (ostium vaginae) instead and in this case, the interlabial pad 10 can be fitted deep inside the ostium vaginae. Also the number of fingers to be set on the interlabial pad does not have to be one and, for example, three fingers may be set along the interlabial pad 10. Specifically, the feel of the index finger and the fourth finger may be made to be transmitted to the respective labia while inserting the interlabial pad onto the vestibular floor with the middle finger. In this case, the transmitting region 20 is the region along which the index finger and fourth finger are set.

[Effects]

As described above, with the interlabial pad 10 of the present embodiment, since, when a pressing pressure of a finger is applied from the opposite body side face of the interlabial pad 10 in the fitting process, the finger sinks in more readily and the thickness becomes thinner at the transmitting region 20 than at the other regions 21, the feel of the finger 31 can be transmitted to the ostium vaginae 33 more definitely and readily. The ostium vaginae 33 can thus be found readily and the interlabial pad 10 can be fitted definitely and easily at an appropriate position of the labia 32.

Modification Example of the First Embodiment

Figure 7:
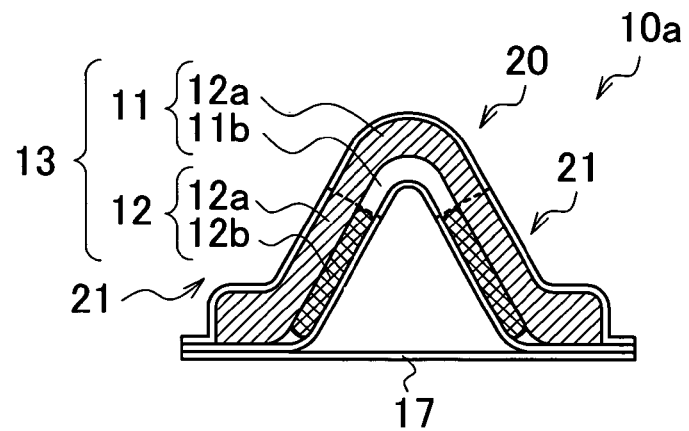
FIG. 7 is a sectional view of an interlabial pad 10a of a modification example of the first embodiment as sectioned in the lateral direction.

A modification example of the interlabial pad 10 of the first embodiment has a structure wherein a space is provided inside the first absorbent 11 at the transmitting region 20. FIG. 7 is a sectional view of an interlabial pad 10a of this modification example as sectioned in the lateral direction. With this interlabial pad 10a, each of the second absorbents 12 at the other regions 21 has the two layers of an upper layer absorbent 12a and a lower layer absorbent 12b. Meanwhile, the first absorbent 11 at the transmitting region 20 has the upper layer absorbent 12a and, instead of the lower layer absorbent 12b, has a space 11b. As the upper layer absorbent 12a, a mixture of 85% rayon and 15% natural cotton is used, and as the lower layer absorbent 12b, pulp is used. The transmitting region 20 and the other regions 21 have an embossed area percentage of 1%. Also, whereas the LC value of the transmitting region 20 is 0.41, the LC value of the other regions 21 is 0.47, and the difference between the LC values of these regions is 0.06.

[Actions and Effects]

Figure 8:
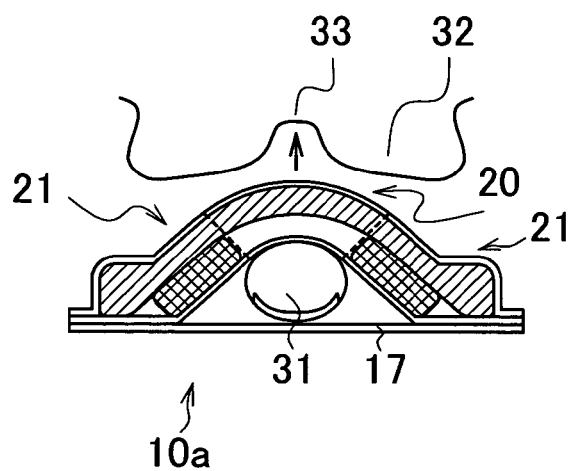
FIG. 8 is a partially sectional view showing a manner in which the interlabial pad 10a of the modification example of the first embodiment is about to be fitted between labia as viewed from the buttocks side of a wearer.
Figure 9:
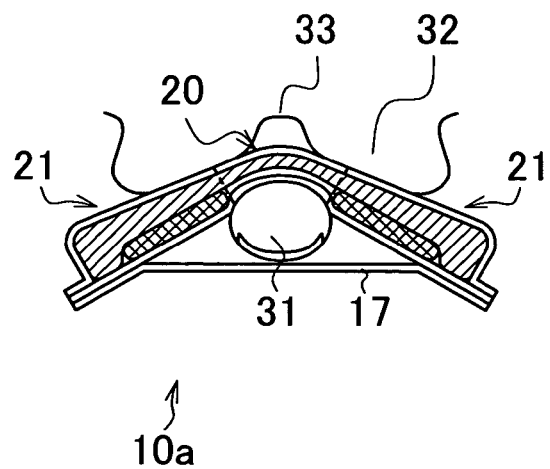
FIG. 9 is a partially sectional view showing a manner in which the interlabial pad 10a of the modification example of the first embodiment is pushed in between labia as viewed from the buttocks side of a wearer.

FIG. 8 is a partially sectional view showing the state, in which a wearer has a finger 31 set on the interlabial pad 10a of the modification example and is about to fit the interlabial pad 10a onto the labia 32, as viewed from the buttocks side of a wearer. In this interlabial pad 10a, since the first absorbent 11 at the transmitting region 20 has the space 11b, the finger 31 sinks in adequately due to the collapsing of the space 11b by the pressing pressure of the finger 31, and since the first absorbent 11 at the transmitting region 20 is smaller in LC value than the second absorbents 12 at the other regions 21 and is more readily compressed, the thickness of the transmitting region 20 becomes thin. The state in which this occurs as viewed from the buttocks side of the wearer is shown in the partially sectional view of FIG. 9. Thus in this interlabial pad 10a, since, when the pressing pressure of the finger 31 is applied from the opposite body side face in the fitting process, the thickness of the transmitting region 20 becomes thinner, the feel of the finger can be transmitted to the ostium vaginae 33 definitely. The ostium vaginae 33 can thus be found easily and the interlabial pad 10a can be fitted definitely and readily at an appropriate position of the labia 32.

Second Embodiment

The interlabial pad 10b according to a second embodiment has a structure wherein the first absorbent 11 in the transmitting region 20 of the interlabial pad 10 of the first embodiment is made more easily bendable than the second absorbents 12 in the other regions 21.

[Transmitting Region]

The first absorbent in the transmitting region 20 of the interlabial pad 10b according to this embodiment is made small in the value of B so that it can be bended more easily than the second absorbents in the other regions 21. Specifically, as the first absorbent at the transmitting region 20, an absorbent, which is a mixture of 85% rayon and 15% natural cotton, has a basis weight per unit area of 180 g/m$^2$, and has been embossed to an embossed area percentage of 1%, is used, and as each of the second absorbents in the other regions 21, a 100% pulp absorbent, having a basis weight per unit area of 360 g/m$^2$ and embossed to an embossed area percentage of 1%, is used. Whereas the B value of the first absorbent in the transmitting region 20 is 0.77, the B value of the second absorbents in the other regions 21 is 3.92, and the difference between the B values of the respective regions is 3.15.

Each of these B values is a value measured in compliance to a measurement method by KES system and is measured using a "KES Bend Characteristics" measuring device made by Kato Tech Co., Ltd. and under the condition of a bend curvature of 0.2 g/cm$^{-1}$ and using a 40 mm chuck. Each sample had a measured width of 10 mm and a length in the chuck direction of approximately 50 mm. The sampling position of a test piece shall now be described. The sampling position for a test piece for the transmitting region 20 is a region, which spans the longitudinal direction central axis and comes in contact with the ostium vaginae, and the sampling position for a test piece for the other regions 21 is a region in the periphery of the transmitting region 20. In the case where the interlabial pad 10 is folded in two, the measurement is carried out in the state in which the interlabial pad 10 is unfolded.

[Actions and Effects]

Figure 10:
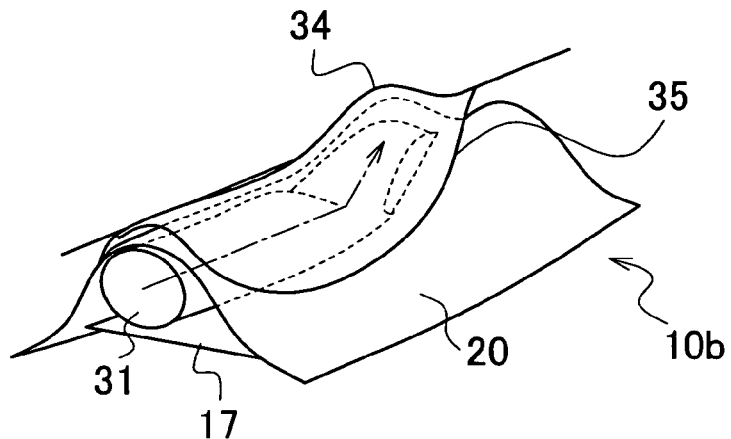
FIG. 10 is a perspective view schematically showing how readily an interlabial pad 10b of a second embodiment can bend in the longitudinal direction.

The transmitting region 20 of the present interlabial pad 10b is easily bendable in both the longitudinal and lateral directions. FIG. 10 is a perspective diagram showing how easily the interlabial pad 10b of the present embodiment can bend in the longitudinal direction when a wearer sets a finger 31 in order to fit the interlabial pad 10b onto the labia. Since the interlabial pad 10b is thus easily bendable in the longitudinal direction, it takes on a structure with which the shape of the finger 31 can be aligned readily with the recessed shape of the ostium vaginae and can be fitted on without rubbing of the labia.

Figure 11:
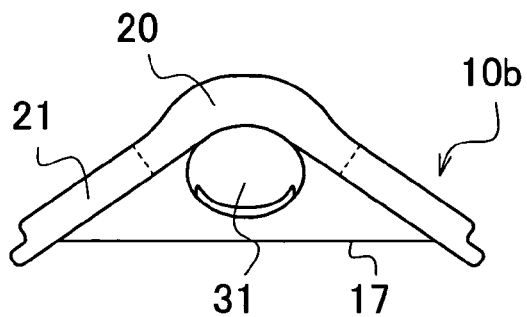
FIG. 11 is a view showing how readily the interlabial pad 10b of the second embodiment can bend in the lateral direction.

FIG. 11 is a diagram showing how easily the interlabial pad 10b of the present embodiment can be bent in the lateral direction when a wearer sets a finger 31 in order to fit the interlabial pad 10b onto the labia. Since the interlabial pad 10b is thus easily bendable in the lateral direction as well, the interlabial pad 10b can be made to adequately follow the shape and movement of the finger 31 in the process of guiding the interlabial pad 10b between the labia with the finger 31 set thereon. Thus in this interlabial pad 10b, since the feel of the finger 31 can be transmitted to the ostium vaginae definitely, the ostium vaginae can be found easily and the interlabial pad 10b can be fitted on definitely and readily at an appropriate position between the labia. Also, the formation of gaps between the finger 31 and the opposite body side face of the interlabial pad 10b can be prevented and deviations will therefore not occur between the finger 31 and the interlabial pad 10b due to impact in the fitting process.

Modification Example 1 of the Second Embodiment

[Transmitting Region]

Figure 12:
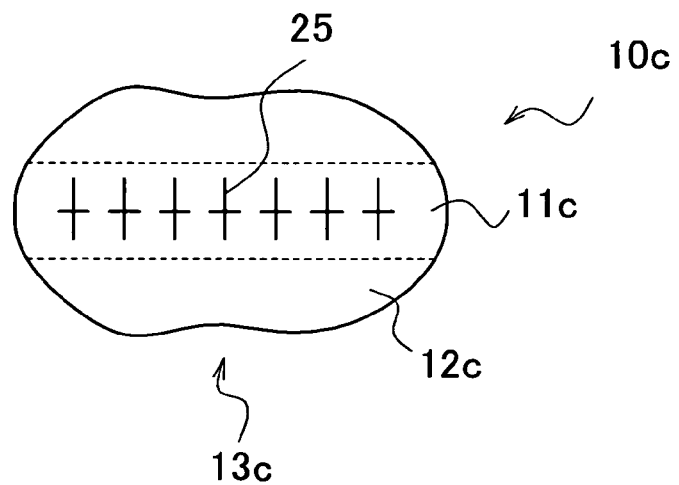
FIG. 12 is a plan view of an absorbent 13c of an interlabial pad 10c of a Modification Example 1 of the second embodiment.

A Modification Example 1 of the interlabial pad 10b of the second embodiment has a structure wherein the first absorbent 11 in the transmitting region 20 of the interlabial pad 10 is provided with slits. FIG. 12 is a plan view of an absorbent 13c of an interlabial pad 10c of this Modification Example 1. The absorbent 13c is composed of the first absorbent 11 and the second absorbents. As to slits 25 provided in the first absorbent 11c in the transmitting region 20 of the interlabial pad 10c of the present Modification Example 1, a slit pattern, directed in the longitudinal direction, is intersected with a slit pattern, directed in the lateral direction. The length of each slit is 10 mm, the interval between slits is 10 mm, and these slits are formed to pierce through in the thickness direction of the absorbent 13c.

[Actions and Effects]

Since slits 25, with which the slit pattern, directed in the longitudinal direction, is intersected with the slit pattern, directed in the lateral direction, are thus provided in the first absorbent 11c at the transmitting region 20 in the interlabial pad 10c of the Modification Example 1, bending in both the longitudinal and lateral directions can be carried out easily, so that the interlabial pad 10c thus follows the shape and movement of a finger of a wearer, enabling the definite transmission of the feel of the finger to the ostium vaginae. The ostium vaginae can thus be found easily and the interlabial pad 10c can be fitted on definitely and readily at an appropriate position between the labia.

Modification Example 2 of the Second Embodiment

[Transmitting Region]

Figure 13:
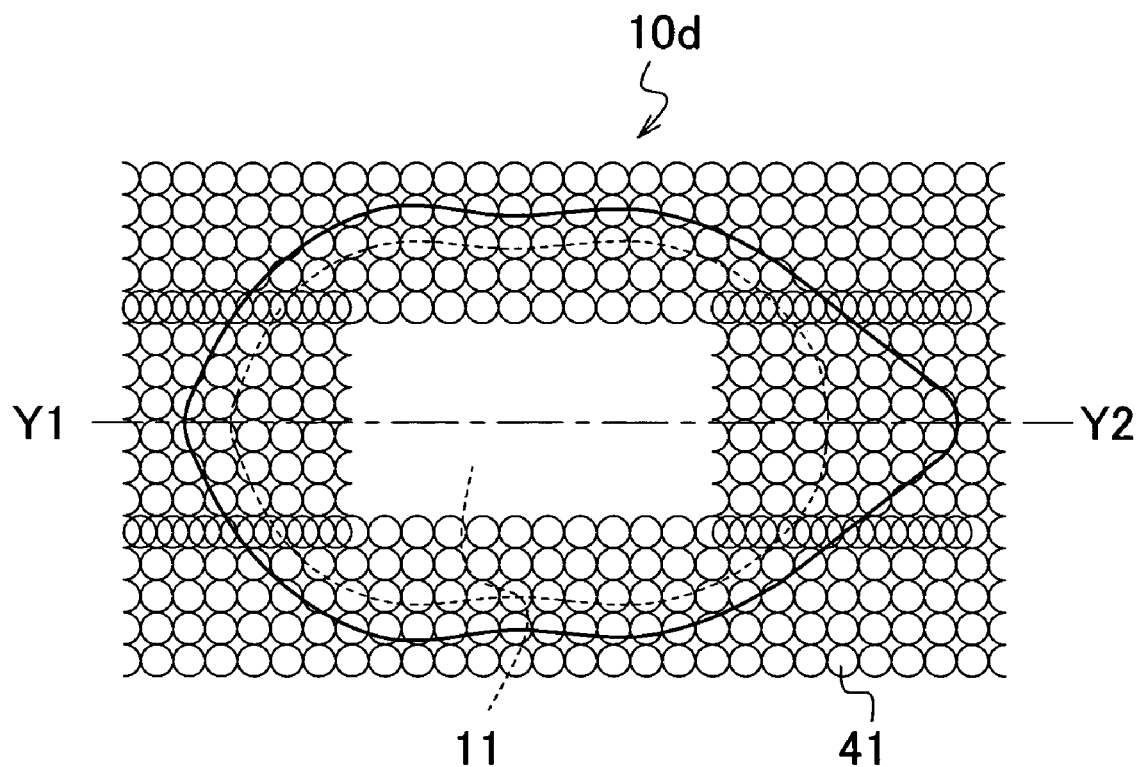
FIG. 13 is a plan view for describing the adhesion state of an interlabial pad 10d of a Modification Example 2 of the second embodiment.
Figure 14:
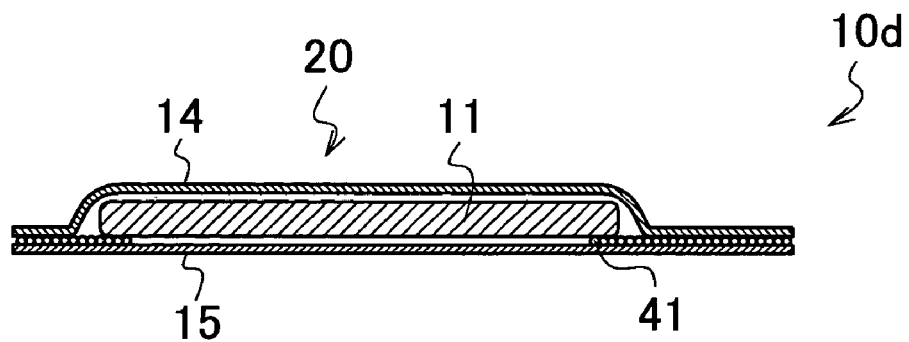
FIG. 14 is a sectional view of the interlabial pad 10d of FIG. 13 as sectioned in the Y1-Y2 direction.

In a Modification Example 2 of the interlabial pad 10b of the second embodiment, the first absorbent 11 at the transmitting region 20 of the interlabial pad 10b of the second embodiment is not joined to the surface side sheet 14 and only a part thereof is joined by hot melting to the back face side sheet 15. FIG. 13 is a plan view for illustrating the adhesion state of an interlabial pad 10d of the Modification Example 2, which is a diagram showing the bonding pattern of hot melt 41 as well. FIG. 14 is a sectional view of the interlabial pad 10d of FIG. 13 as sectioned in the Y1-Y2 direction. As shown in these FIGS. 13 and FIG. 14, a central part of the first absorbent 11 at the transmitting region 20 of the interlabial pad 10d is not joined by the hot melt 41 and only the edges are joined to the back face side sheet 15.

[Actions and Effects]

Thus in the interlabial pad 10d of the Modification Example 2, since the first absorbent 11 at the transmitting region 20 is not bonded to the surface side sheet 14 and only a part of the first absorbent 11 and the back face side sheet 15 are bonded, these respective members, the first absorbent 11, surface side sheet 14, and back face sheet 15 are enabled to move independently and the interlabial pad 10d is thus made easily bendable as a whole. The interlabial pad 10d thus follows the shape and movement of a finger to enable the feel of the finger to be transmitted definitely to the ostium vaginae without fail. The ostium vaginae can thus be found easily and the interlabial pad 10d can be fitted on definitely and readily at an appropriate position between the labia.

Third Embodiment

[Transmitting Region]

In the interlabial pad of according to this embodiment, the transmitting region 20 of the interlabial pad 10 of the first embodiment is made higher in the thermal conductivity than the other regions 21. Specifically, whereas pulp is used as the second absorbents 12 in the other regions 21, polyethylene, which is higher in thermal conductivity than pulp, is used as the first absorbent 11 at the transmitting region 20.

[Actions and Effects]

Since the transmitting region of the interlabial pad according to this embodiment is thus made higher in the thermal conductivity than the other regions and since the body temperature of a finger at the transmitting region can thus be transmitted to the ostium vaginae when a pressing pressure by the finger is applied from the opposite body side face in the fitting process, the interlabial pad can be fitted on definitely and easily at an appropriate position between the labia.

Fourth Embodiment

[Transmitting Region]

Figure 15:
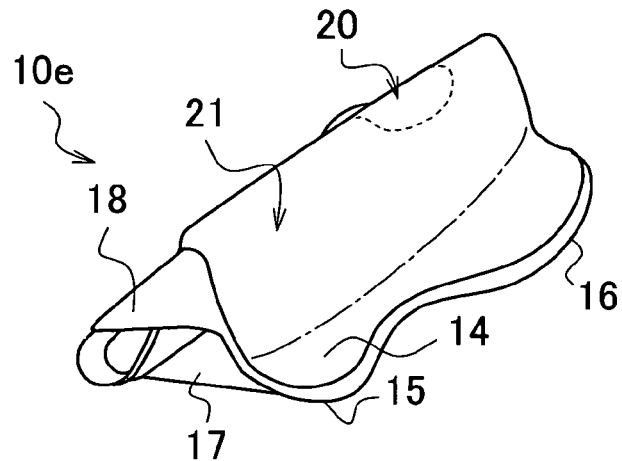
FIG. 15 is a perspective view of an interlabial pad 10e of a fourth embodiment.

FIG. 15 is a perspective view of an interlabial pad 10e according to this embodiment. In the interlabial pad 10e of this embodiment, the transmitting region 20 of the interlabial pad 10 of the first embodiment is positioned at one side in the longitudinal direction so as to be biased towards the side facing the buttocks when the interlabial pad is fitted on. Specifically, the transmitting region 20 is positioned within the range from 10% to 50% of the total length in the longitudinal direction from the end part at the side facing the buttocks when the interlabial pad is fitted on.

[Actions and Effects]

In the present embodiment, since the transmitting region 20 is positioned at one side in the longitudinal direction so as to be biased towards the side facing the buttocks when the interlabial pad is fitted on, the interlabial pad 10e can be fitted smoothly onto the ostium vaginae, which exists at the rearmost part between the labia as viewed from a wearer. Also, since the region of the interlabial pad 10e that is exposed from the rear of the labia as viewed from a wearer can be lessened, the falling off of the interlabial pad 10e from between the labia can be prevented, and consequently, the leakage of menstrual blood can be reduced.

Fifth Embodiment

[Transmitting Region]

Figure 16:
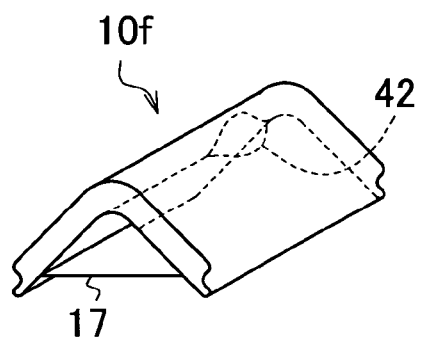
FIG. 16 is a perspective view of an interlabial pad 10f of a fifth embodiment.

FIG. 16 is a perspective view of an interlabial pad 10f according to a fifth embodiment. The interlabial pad 10f of this embodiment has a structure wherein an indentation 42 is provided on the opposite body side face of the transmitting region 20. In this case, the indentation 42 has a depth of 2 mm.

[Actions and Effects]

In this interlabial pad 10f, when a wearer sets a finger along the opposite body side face in the fitting process, the finger can easily find the indentation 42 so as to be guided to the transmitting region 20. The feel of the finger can thus be transmitted easily to the ostium vaginae and the interlabial pad 10f can be fitted on definitely and readily at an appropriate position between the labia.

Sixth Embodiment

[Transmitting Region]

Figure 17:
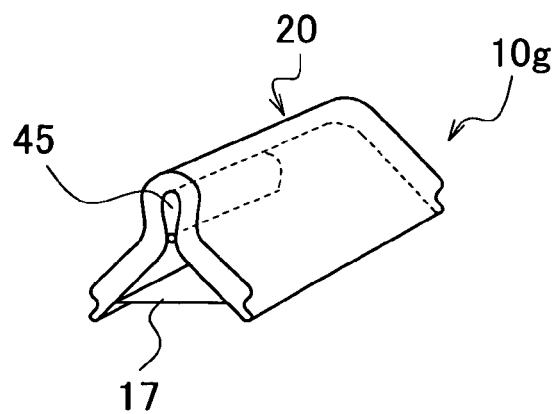
FIG. 17 is a perspective view of an interlabial pad 10g of a sixth embodiment.
Figure 18:
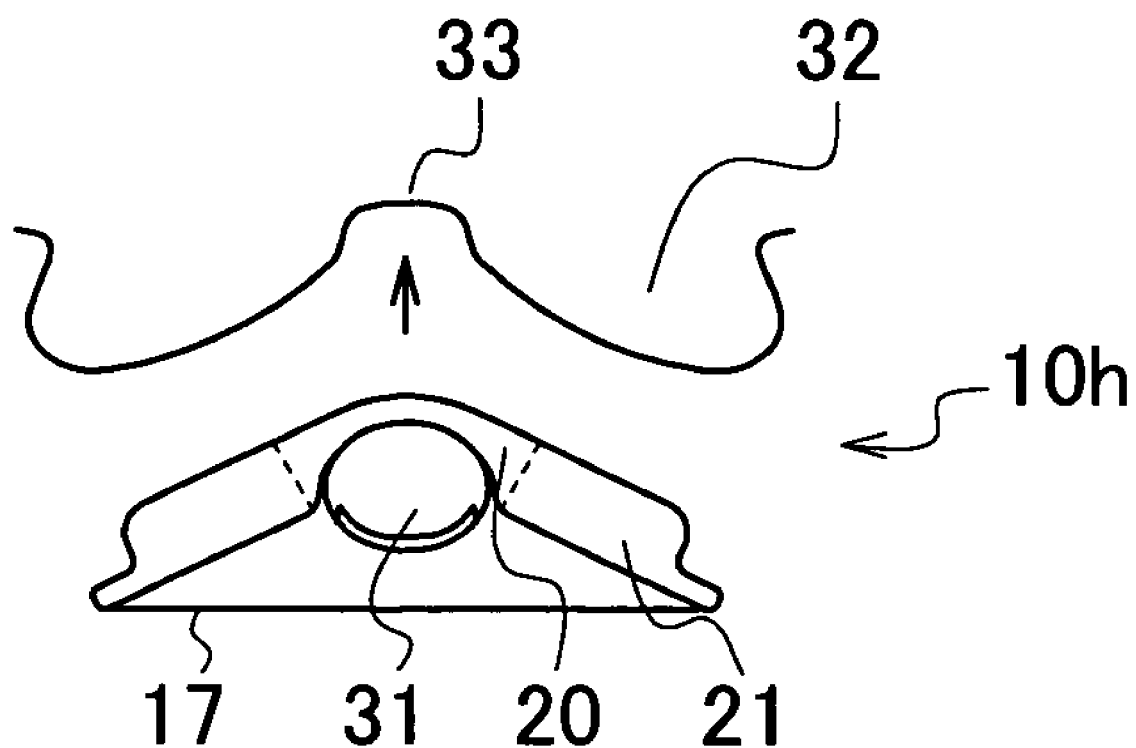
FIG. 18 is a partially sectional view showing the manner in which an interlabial pad 10h is about to be fitted between labia as viewed from the buttocks side of a wearer.

FIG. 17 is a perspective view of an interlabial pad 10g according to a sixth embodiment. The interlabial pad 10g of this embodiment has a joined region 45, in which the inside areas of the opposite body side face of the interlabial pad 10 of the first embodiment are joined each other across a predetermined length along the longitudinal central axis at a predetermined distance away from a crease, and the transmitting region 20 is positioned in a region in which the inside areas of the opposite body side face are not joined each other. The region in which the inside areas of the opposite body side face are not joined each other is positioned so as to be biased towards the side in the longitudinal direction that faces the buttocks in the fitting process.

[Actions and Effects]

In this interlabial pad 10g, since a step forms at the boundary between the joined region 45 and non-joined region, when a wearer sets a finger on the opposite body side face in the fitting process, the finger can find easily the step so as to be guided to the transmitting region. Since the feel of the finger can thus be transmitted definitely to the ostium vaginae, the ostium vaginae can be found easily and the interlabial pad 10g can be fitted on accurately and readily at an appropriate position between the labia. Furthermore, since the position at which the inside areas opposing the body side are joined each other is separated from the crease by a predetermined distance so that a space is formed between the crease and the joined position, external pressures, which are generated against the interlabial pad 10g while it is fitted on, can be cushioned by this space and the wearer will thus hardly feel a foreign object sensation.

What is claimed is:

1. An interlabial pad, having a body side face oriented towards a body side, and an opposite body side face oriented towards a side opposite to the body side face, being substantially formed to a longitudinal shape having a longitudinal direction and a lateral direction, and to be fitted between labia by a wearer setting a finger on the opposite body side face along the longitudinal direction in a fitting process, the interlabial pad comprising:

a surface side sheet positioned at the body side face;
   a back face side sheet positioned at the opposite body side face;
   an absorbent which has a predetermined thickness and absorbs and holds body fluids, being provided between the surface side sheet and the back face side sheet; and
   a transmitting region provided between the surface side sheet and the back face side sheet and provided on at least part of a region located adjacent to a central axis in the longitudinal direction, the transmitting region transmitting a sensation of a touch of the finger to the wearer's body in a thickness direction of the interlabial pad, and the transmitting region having a portion which has a value of linearity of a compression characteristic in a range from 0.10 to 0.50 that is lower in the value of linearity of a compression characteristic and is more easily compressed in the thickness direction by a pressing pressure of the wearer's finger than other regions that are peripheral regions of the transmitting region, wherein a difference in the values of linearity of the compression characteristic between the transmitting region and the other regions that are peripheral regions of the transmitting region is in a range from 0.05 to 0.50.

2. The interlabial pad according to claim 1, wherein the width along the lateral direction of the transmitting region is in a range from 5 mm to 70 mm.

3. The interlabial pad according to claim 1, wherein the transmitting region is lower in a basis weight per unit area of the absorbent than the other regions that are peripheral regions of the transmitting region.

4. The interlabial pad according to claim 1, wherein in the transmitting region, the absorbent has a space therein so as to be easily compressible.

5. The interlabial pad according to claim 1, wherein the transmitting region is smaller in the value of flexural rigidity and can be bent more easily by the pressing pressure of the wearer's finger than the other regions that are peripheral regions of the transmitting region.

6. The interlabial pad according to claim 1, wherein the difference in the flexural rigidity value between the transmitting region and the flexural rigidity value of the other regions that are peripheral regions of the transmitting region is in a range from $0.50\times10^{-4}$ (N·m$^2$/m) to $5.00\times10^{-4}$ (N·m$^2$/m).

7. The interlabial pad according to claim 1, wherein the transmitting region has slits that are provided in the absorbent and directed in the longitudinal direction and in the lateral direction, the slits directed in the longitudinal direction being intersected with the slits directed in the lateral direction.

8. The interlabial pad according to claim 1, wherein the transmitting region is a portion where
   the absorbent and the back face side sheet are in a state of being free of each other at least in part.

9. The interlabial pad according to claim 1, wherein the transmitting region is higher in thermal conductivity than the other regions that are peripheral regions of the transmitting region.

10. The interlabial pad according to claim 9, wherein the transmitting region contains at least one of a material selected from copper, aluminum, diamond and carbon.

11. The interlabial pad according to claim 9, wherein the transmitting region includes synthetic fibers.

12. The interlabial pad according to claim 11, wherein the synthetic fibers are polyethylene fibers.

13. The interlabial pad according to claim 10, wherein the transmitting region contains a crushed carbon.

14. The interlabial pad according to claim 1, wherein the transmitting region has an indentation directed towards the body side face, provided on the opposite body side face.

15. The interlabial pad according to claim 1, wherein the interlabial pad is folded in two along a crease extending along the longitudinal direction central axis, so that inside areas of the opposite body side face are facing each other and joined across a predetermined length along the central axis at a predetermined distance away from the crease, and the transmitting region is positioned in a region in which the inside areas of the opposite body side face are separated from each other.

16. The interlabial pad according to claim 1, wherein the interlabial pad is an interlabial pad for urinary incontinence.

17. The interlabial pad according to claim 1, wherein the interlabial pad is an interlabial pad for absorbing vaginal discharge.

18. The interlabial pad according to claim 5, wherein the flexural rigidity value in the transmitting region is in a range from $0.20 \times 10^{-4}$ (N·m$^2$/m) to $3.00 \times 10^{-4}$ (N·m$^2$/m) and the flexural rigidity value of the other regions that are peripheral regions of the transmitting region is in a range from $2.00 \times 10^{-4}$ (N·m$^2$/m) to $5.00 \times 10^{-4}$ (N·m$^2$/m).

* * * * *